(12) United States Patent
Brunnarius et al.

(10) Patent No.: US 9,655,732 B2
(45) Date of Patent: May 23, 2017

(54) JOINT PROSTHESIS ATTACHMENT SYSTEM, DEVICE AND METHOD

(71) Applicant: Biomet France SARL, Valence (FR)

(72) Inventors: Yann Brunnarius, Chatuzange le Goubet (FR); Pierric Deransart, Grenoble (FR)

(73) Assignee: Biomet France Sarl, Valence (FR)

( * ) Notice: Subject to any disclaimer, the term of this patent is extended or adjusted under 35 U.S.C. 154(b) by 36 days.

(21) Appl. No.: 14/511,967

(22) Filed: Oct. 10, 2014

(65) Prior Publication Data

US 2015/0032214 A1    Jan. 29, 2015

Related U.S. Application Data

(62) Division of application No. 12/765,347, filed on Apr. 22, 2010, now Pat. No. 8,858,640.

(30) Foreign Application Priority Data

Apr. 22, 2009 (FR) ........................................ 95 2635

(51) Int. Cl.
*A61F 2/40* (2006.01)
*A61F 2/30* (2006.01)
*A61B 17/86* (2006.01)

(52) U.S. Cl.
CPC ........ *A61F 2/4081* (2013.01); *A61F 2/30734* (2013.01); *A61B 17/86* (2013.01); *A61F 2002/30332* (2013.01); *A61F 2002/30604* (2013.01); *A61F 2220/0033* (2013.01)

(58) Field of Classification Search
CPC .................................................... A61F 2/4081
See application file for complete search history.

(56) References Cited

U.S. PATENT DOCUMENTS

| 5,593,448 | A | 1/1997 | Dong |
| 5,658,341 | A | 8/1997 | Delfosse |
| 5,800,551 | A | 9/1998 | Williamson et al. |

(Continued)

FOREIGN PATENT DOCUMENTS

| EP | 1402853 A2 | 3/2004 |
| EP | 1639967 A1 | 3/2006 |

(Continued)

OTHER PUBLICATIONS

Comprehensive Naon Stemless Shoulder Anatomic and Reverse. Surgical Technique brochure. Biomet® Orthopedics. (2012) pp. 1-60.

(Continued)

*Primary Examiner* — Brian Dukert
(74) *Attorney, Agent, or Firm* — Schwegman Lundberg & Woessner, P.A.

(57) ABSTRACT

Prosthetic systems, devices, and methods for attaching prosthetic joint components to a vault-shaped portion of the anatomy. A device for attaching a glenoid joint component for a shoulder prosthesis to a glenoid cavity includes a body adapted to extend into the cortical bony vault of the glenoid cavity for supporting the glenoid joint component and a plurality of contact arms secured to the body and projecting outwardly from a central longitudinal axis of the body to define contact surfaces for engaging an internal face of a peripheral wall of a glenoid vault.

19 Claims, 6 Drawing Sheets

(56) References Cited

U.S. PATENT DOCUMENTS

| | | |
|---|---|---|
| 8,858,640 B2 | 10/2014 | Brunnarius et al. |
| 2003/0055507 A1 | 3/2003 | McDevitt et al. |
| 2005/0261775 A1 | 11/2005 | Baum et al. |
| 2007/0150065 A1* | 6/2007 | Angibaud ............... A61F 2/389 623/20.14 |
| 2007/0260321 A1 | 11/2007 | Stchur |
| 2010/0114326 A1 | 5/2010 | Winslow et al. |
| 2010/0274359 A1 | 10/2010 | Brunnarius et al. |

FOREIGN PATENT DOCUMENTS

| | | |
|---|---|---|
| EP | 1639967 B1 | 7/2008 |
| EP | 1402853 B1 | 5/2010 |

OTHER PUBLICATIONS

European Search Report issued in EP Application No. 10160400 dated Aug. 23, 2010, 4 pages.

"U.S. Appl. No. 12/765,347, Final Office Action mailed Apr. 4, 2014", 11 pgs.

"U.S. Appl. No. 12/765,347, Final Office Action mailed Jul. 3, 2012", 13 pgs.

"U.S. Appl. No. 12/765,347, Non Final Office Action mailed Jan. 6, 2012", 13 pgs.

"U.S. Appl. No. 12/765,347, Non Final Office Action mailed Sep. 18, 2013", 12 pgs.

"U.S. Appl. No. 12/765,347, Notice of Allowance mailed Jun. 13, 2014", 5 pgs.

"U.S. Appl. No. 12/765,347, Response filed Jan. 21, 2014 to Non Final Office Action mailed Sep. 18, 2013", 13 pgs.

"U.S. Appl. No. 12/765,347, Response filed Apr. 6, 2012 to Non Final Office Action mailed Jan. 6, 2012", 9 pgs.

"U.S. Appl. No. 12/765,347, Response filed Jun. 4, 2014 to Final Office Action mailed Apr. 4, 2014", 7 pgs.

"U.S. Appl. No. 12/765,347, Response filed Aug. 2, 2013 to Final Office Action mailed Jul. 3, 2012", 14 pgs.

"U.S. Appl. No. 12/765,347, Response filed Nov. 16, 2011 to Restriction Requirement mailed Oct. 28, 2011", 2 pgs.

"U.S. Appl. No. 12/765,347, Restriction Requirement mailed Oct. 28, 2011", 9 pgs.

\* cited by examiner

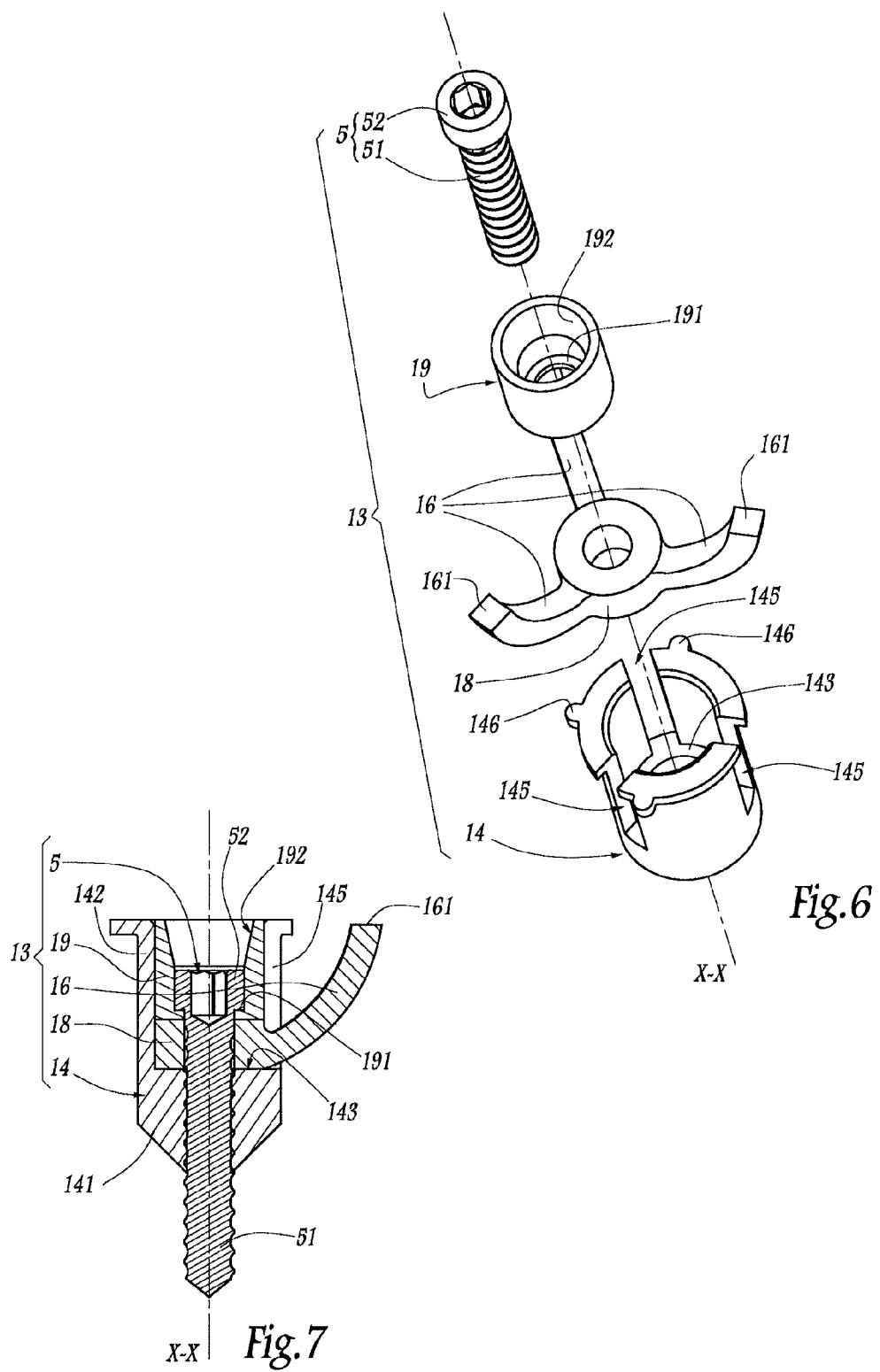

JOINT PROSTHESIS ATTACHMENT SYSTEM, DEVICE AND METHOD

CROSS-REFERENCE TO RELATED APPLICATIONS

This application is a divisional of U.S. patent application Ser. No. 12/765,347 filed on Apr. 22, 2010, which claims benefit of French Patent Application No. 952635 filed on Apr. 22, 2009. The entire disclosures of each of the above applications are incorporated herein by reference.

FIELD

The present disclosure relates to a joint prosthesis attachment system, device, and method.

BACKGROUND

This section provides background information related to the present disclosure which is not necessarily prior art.

One of the causes of failure or complication with shoulder arthroplasty is connected with poor attachment of the glenoid prosthetic body to the glenoid cavity. When the glenoid cavity of a patient undergoing surgery is worn and/or has an impaired bony makeup, the surgeon has difficulty firstly in correctly positioning the glenoid prosthetic body in relation to the glenoid cavity, so as to give the joint face of this component a retroversion angle that is identical to, or at the very least, is as close as possible to, the anatomical retroversion of the original glenoid cavity of the patient and secondly in firmly attaching the prosthetic body to the glenoid cavity, to ensure that the attachment is sufficiently strong. An attachment that is ill-positioned and/or not strong enough leads to wear and/or detachment of the glenoid prosthetic body.

This being the case, U.S. Pat. Nos. 5,800,551 and 5,593, 448, and U.S. Application Publication 2003/0055507 propose equipping the opposite face of the glenoid joint component to the joint face thereof with several projecting pegs designed to be driven into spongy bony matter with which the glenoid fossa of a patient undergoing surgery is filled. If appropriate, the glenoid fossa is filled to such a point that one or some of the pegs press via their free end against the closed end of the cortical bony vault of the glenoid cavity. In practice, positioning these pegs in relation to the glenoid cavity remains tricky when the glenoid cavity is worn. Further, inasmuch as the transmission of load between the free end of the pegs and the glenoid cavity is necessarily limited, there is a need to ensure that the periphery of the glenoid joint component is positioned resting against the end edge, that faces towards the humerus, of the vault of the glenoid cavity which procedure, in the long term, weakens this end edge by creating rims and causes the glenoid joint component to become detached.

EP 1 639 967 for its part considers providing the opposite face of the glenoid joint component to its joint face with a solid projecting anchor, in the overall form of a cone frustum, to rest laterally against the wall of the vault of the glenoid cavity, occupying the entire internal volume of the glenoid fossa. This solution prevents any bone regrowth in the fossa and soon leads to necrosis of the glenoid cavity, especially when, as before, the periphery of the glenoid joint component is designed to rest against the end border of the vault of the glenoid cavity.

SUMMARY

This section provides a general summary of the disclosure, and is not a comprehensive disclosure of its full scope or all of its features.

Various aspects of embodiments provided herein relate to prosthetic systems, devices, and methods for attaching prosthetic joint components to a vault-shaped portion of the anatomy.

Some aspects relate to devices for attaching a glenoid prosthetic component to a glenoid cavity, even when the cavity is worn, where a strong connection to the glenoid cavity is provided otherwise unnecessarily damaging the bony makeup of the cavity.

In some embodiments, the device includes a body for supporting the glenoid joint component and three contact arms that outstretch from the body to contact an internal face of a peripheral wall of the vault, or perimeter of the vault. The device according to some embodiments utilizes a geometric shape and mechanical integrity of the perimeter of the vault to secure the device while substantially reducing or preventing adverse affects on the biological environment of the vault, including avoiding restriction of blood supply to biological environment of the vault.

In some embodiments, the contact arms rest transversely against an internal face of the peripheral wall of the vault of the glenoid cavity to contact cortical bony matter making up that perimeter. With this perimeter contact, a particularly strong anchorage is provided without substantial damage to the glenoid cavity. For example, the contact arms are mechanically supported by the body, where the body is adapted to help center the device in the glenoid fossa, (e.g., even if the glenoid cavity of the patient undergoing surgery is worn). In some embodiments, the body is adapted to run substantially along the central geometric axis of revolution associated with the fossa once secured to the vault. Spaces between the arms optionally help facilitate flow of biological fluids to the fossa so that such fluids are able to reach the closed end of the vault. By facilitating flow of such fluids, bone regrowth in the empty spaces between the arms is promoted, which, in turn, promotes secondary attachment of the device to the vault, for example.

In some embodiments, the body has a central axis along which the body extends inside the vault, and the contact arms extend, or project, transversely from the body and are distributed about the body in a direction peripheral to its axis. Each contact arm has, on its opposite side to the body, a generally convex contact surface pressing against the internal face of the peripheral wall of the vault. In some embodiments, one or more of the contact arms are characterized as follows: at least one of the contact arms is connected rigidly to the body; at least one of the contact arms is connected to the body in a way that is flexible (e.g., through the elastic deformation of material); and/or at least one of the contact arms is adapted to be mechanically articulated relative to the body. For example, in some embodiments, the device is adapted such that at least one of the contact arms is articulable about an ortho-radial axis to the body, or about an axis of rotation that is perpendicular to a radius of the body extending from the longitudinal axis of the body. In some embodiments, the body and at least one of the contact arms are made as one piece. At least two of the contact arms are optionally secured to a carrier which is, in turn, secured to the body. The carrier is optionally housed inside the body which defines through-slots for accommodating the at least two contact arms.

In some embodiments, the body is sized to be housed inside the vault, leaving an empty space around it between the body and the peripheral wall of the vault. The empty space is optionally filled with a spongy bone graft grafted around the body and between the contact arms. In some embodiments, the body is equipped at an end that faces towards an inside of the glenoid cavity with means for fastening into the bone at the closed end of the vault. The opposite end of the body is adapted to be fixedly attached to a glenoid joint component.

Other aspects also relate to a shoulder prosthesis comprising an attachment device and a glenoid joint component borne by a body of the attachment device, the glenoid joint component having on an opposite side to that adjacent the body, a joint face that is generally concave or convex as desired. For example, in some embodiments the shoulder prosthesis has a concave joint face for forming a joint with a convex head of a humerus (the prosthesis being either a hemi-arthroplasty prosthesis if the head of the humerus is natural or a total prosthesis if the head of the humerus is prosthetic). In some other embodiments, the shoulder prosthesis is a reverse total prosthesis where the joint face of the glenoid joint component is convex to form a joint with a concave prosthetic humeral insert.

Another subject of the invention is a surgical method of attaching a glenoid joint component to the glenoid cavity. In some embodiments, the inside of a cortical bony vault of a glenoid cavity is accessed and a support body supporting the glenoid joint component and having three contact arms secured to the body is introduced into the vault. The contact arms are pressed against an internal face of the peripheral wall of the vault. The glenoid joint component is attached to the body, for example using a mechanical fastener or other fastening means.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 is an exploded perspective view of another attachment device, according to some embodiments;

FIG. 7 is a longitudinal section through the device of FIG. 6, in the assembled state.

Corresponding reference numerals indicate corresponding parts throughout the several views of the drawings.

DETAILED DESCRIPTION

Figure 1:
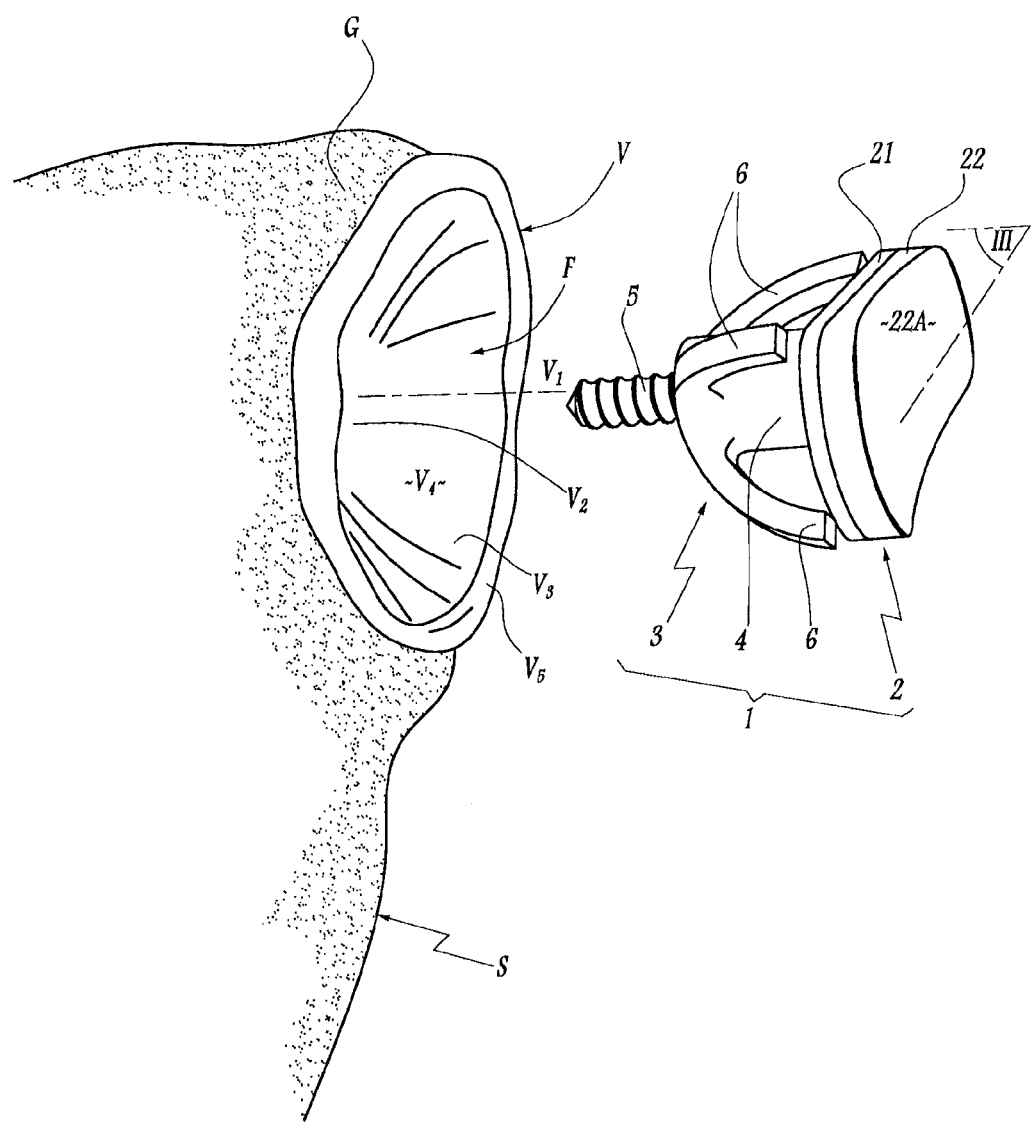
FIG. 1 is a perspective view of a shoulder prosthesis according to the invention, associated with the shoulder blade of a patient undergoing surgery and shown prior to implantation in the shoulder blade, according to some embodiments.

Example embodiments will now be described more fully with reference to the accompanying drawings.

FIGS. 1 to 4 depict a shoulder prosthesis 1 adapted to be implanted in a shoulder blade S of a human being according to some embodiments, although application in other joints and/or other types of animals are contemplated. As shown, the prosthesis 1 comprises a glenoid joint component 2 which, after it has been attached to the glenoid cavity G of the shoulder blade S by a device 3 detailed hereinafter, is able to form a joint with a head, possibly a prosthetic head, of the humerus (not depicted) of the patient undergoing surgery so as to reproduce a joint behavior emulating natural shoulder joint behavior.

As shown in FIGS. 1 to 4, the glenoid joint component 2 comprises a base 21 and a pad 22 according to some embodiments. The base is generally made of metal and the pad of a polymeric material (e.g., polyethylene), although a variety of other materials and material combinations (e.g., ceramics) are contemplated. In some embodiments, one side of the pad 22 is firmly attached to the base 21 (e.g., using mechanical fasteners and/or chemical bonds) and an opposite side of the pad 22 defines a concave face 22A shaped to form a joint with a complementary joint face define by a humeral head (including prosthetic or bone humeral heads) of the patient undergoing surgery.

In some embodiments, the device 3 is designed to anchor the glenoid joint component 2 to the vault V of the glenoid cavity G. The vault V is an anatomical bony structure made up of cortical bone matter. Generally, the cortical bone matter is relatively harder and mechanically stronger bone matter (e.g., in comparison to cancellous bone) having an internal geometry that widens towards the humerus and being centered on the whole on a geometric axis of revolution $V_1$. The vault V is made up of a closed end $V_2$ extended by a peripheral wall $V_3$ of which the internal face $V_4$ is more or less centered on the axis $V_1$, widening gradually from the closed end $V_2$ as far as a border of a free end $V_5$ of the vault V.

Figure 3:
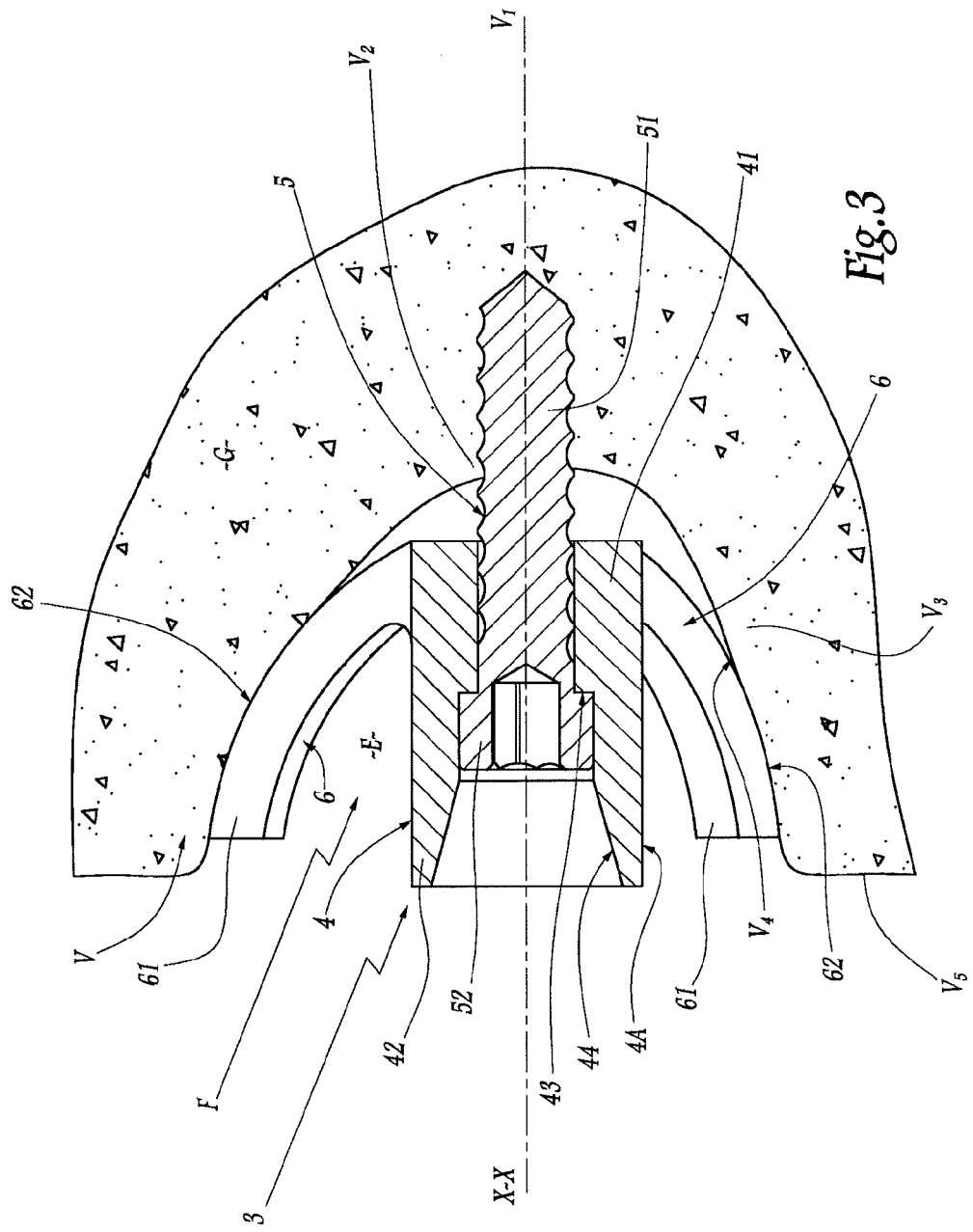
FIGS. 3 and 4 are sections on the plane III of FIG. 1, showing the attachment device belonging to the prosthesis during the process of implantation, and the prosthesis after it has been implanted in the shoulder blade, respectively.
Figure 4:
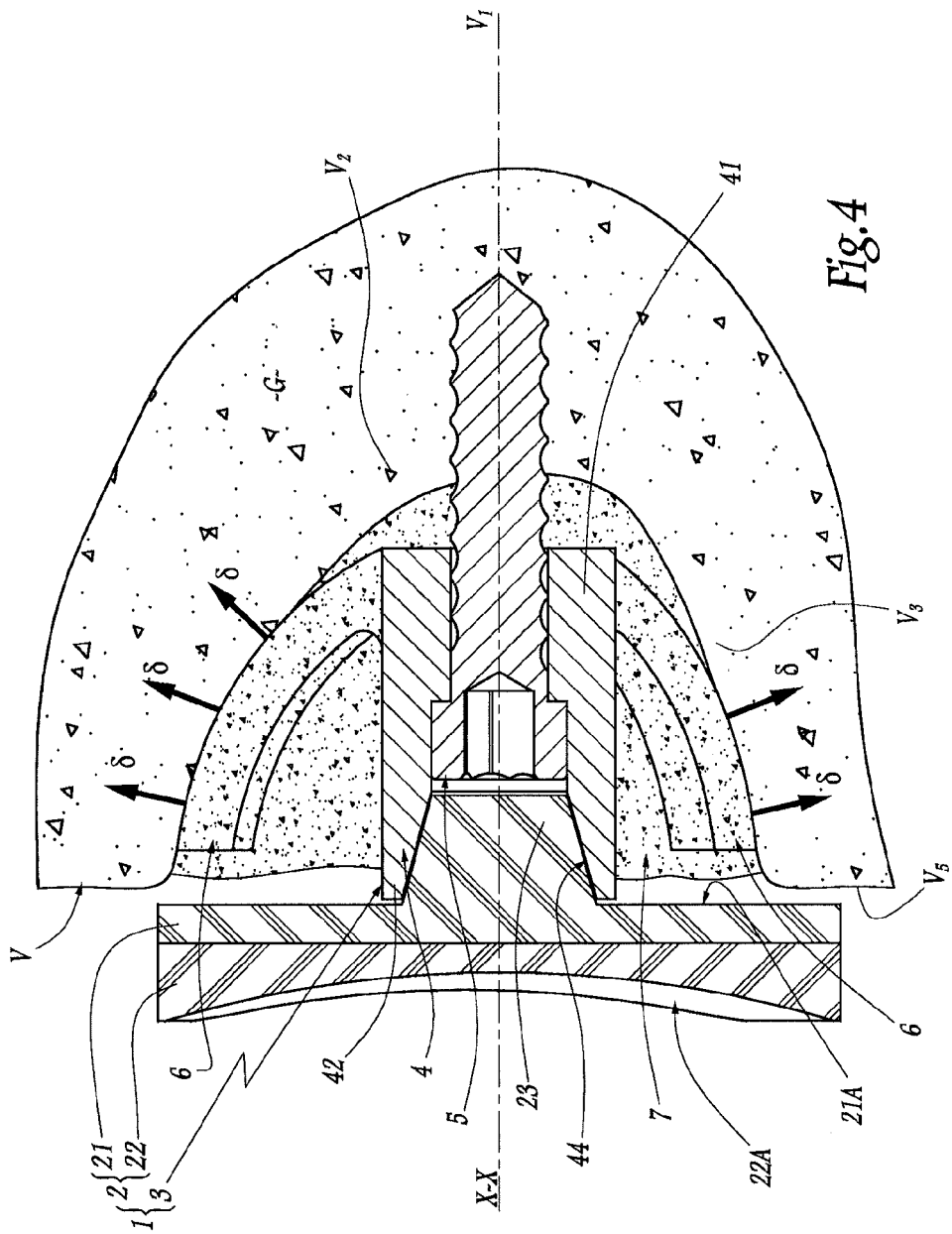

In some embodiments, the attachment device 3 comprises a tubular elongate body 4 and a plurality of contact arms 6. The body 4 is substantially cylindrical and centered on an axis X-X, also described as a central longitudinal axis, the body 4 having an exterior face 4A centered on the axis X-X. The body 4 has first and second longitudinal ends 41, 42 and is sized to be housed in the internal volume of the vault V, including in the fossa F of the glenoid cavity G or glenoid fossa. More specifically, by aligning the axes X-X and $V_1$, the body 4 is optionally placed in the fossa F, extending lengthwise in such a way that the first longitudinal end 41 lies near the closed end $V_2$ of the vault V while the second longitudinal end 42 is situated substantially at the same level, along the axis $V_1$, of the free end $V_5$ of the vault, as shown in FIGS. 3 and 4. When the body 4 is thus housed in the fossa F, the exterior face 4A of the body 4 and the internal face $V_4$ of the vault V define an empty space E between them which extends peripherally around the body 4, as shown in FIG. 3.

In some embodiments, the first end 41 of the body 4 is designed to be firmly attached to the closed end $V_2$ of the vault V by a screw 5 having a shank 51 and a head 52, or other suitable fastening means. In some embodiments, the first end 41 of the body 4 is designed to accommodate the screw 5, centered on the axis X-X, with a portion of the shank 51 of the screw 5 extending through the first end 41 of the body 4 and the remainder of the shank 51 projecting axially from the first end 41 of the body 4. In turn, the head 52 of the screw 5 lies inside the body 4, resting axially against a complementary internal shoulder 43 of the body 4, as shown in FIG. 3.

In some embodiments, the second end 42 of the body 4 is adapted to be fixedly attached to the glenoid joint component 2. For example, as shown, the second end 42 defines a receptacle with a substantially frustoconical interior surface 44, centered on the axis X-X and converging toward the first end 41. Thus, in some embodiments and as shown in FIG. 4, the surface 44 is shaped to accept, in a complementary manner, a frustoconical peg 23 which projects from the face 21A of the base 21 that is opposite the pad 22. In some embodiments, by fitting the peg 23 into the surface 44, the base 21 and, thus, the entire component 2, is immobilized relative to the body 4 as shown in FIGS. 1, 2 and 4.

In some embodiments, the plurality of contact arms 6 are formed as a single unitary piece with the body. As shown, each of the arms 6 projects from the exterior face 4A of the body 4 at the body end 41. The arms 6 each extend lengthwise along the body 4, radially diverging from the axis X-X gradually, starting from the exterior face 4A as far as each of the free ends 61. As shown in FIGS. 1 and 2, each arm 6 has a generally curved longitudinal profile, bulging or splaying out from the body 4. Each arm 6 thus, on its opposite side to the body 4, has a convex surface 62 which, as explained in greater detail, is shaped to rest in a substantially complementary manner against the internal face $V_4$ of the wall $V_3$ of the vault V when the body 4 is housed in the fossa F as shown in FIGS. 3 and 4. In some embodiments, each arm 6 has a substantially square transverse cross section or profile. In other embodiments, each arm is substantially rod like, or cylindrical with a circular cross-section. In some embodiments, the surface 62 is shaped similarly to a portion of a cylinder centered on an axis substantially orthoradial to the axis X-X.

Figure 5:
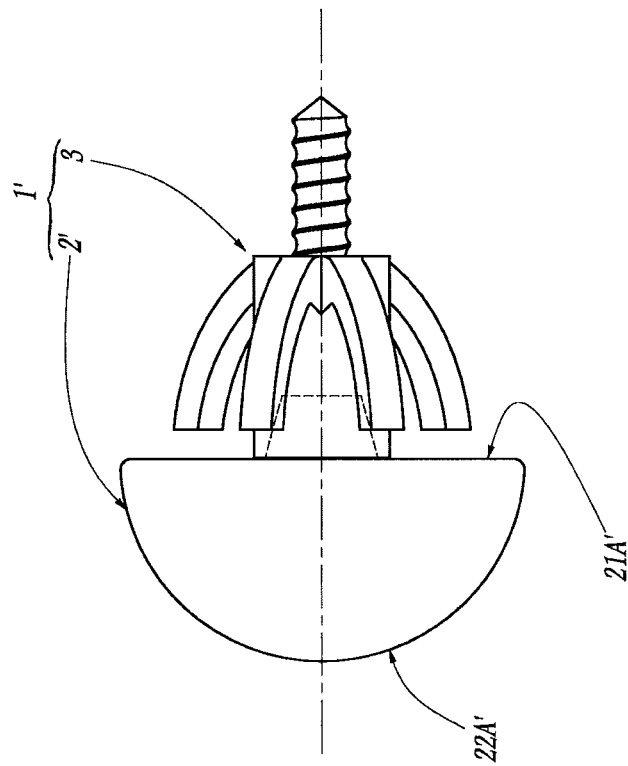
FIG. 5 is an elevation of another embodiment of a shoulder prosthesis, according to some embodiments.
Figure 2:
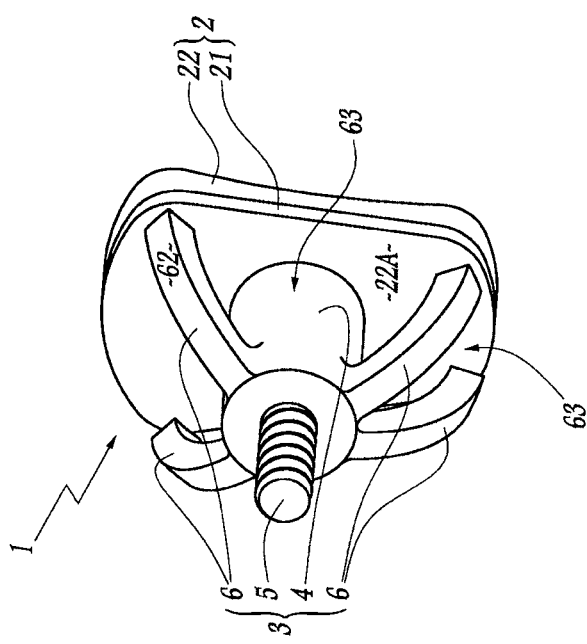
FIG. 2 is a perspective view, from a different viewpoint, of the prosthesis of FIG. 1.

As shown in FIGS. 1, 2, and 5, the four arms 6 are distributed about the body 4, unevenly here, so as to define, between two successive arms 6 around the body 4, an empty passage 63 which runs along the entire length of the exterior face 4A of the body 4, extending between the edges of the first and second ends 41, 42.

Some methods of fitting the shoulder prosthesis 1 are described as follows. In a first phase of a surgical procedure, a surgeon opens access to soft tissue surrounding the glenoid cavity G of the shoulder blade S of a patient, in order to access the vault V and the fossa F, as shown in FIG. 1. If appropriate, the surgeon removes all or some of any remaining spongy bony matter situated in the fossa F, so as to clear access to the internal face $V_4$ of the peripheral wall $V_3$ of the vault V. As an alternative, little if any bony matter is removed and the internal face is compacted at its free surface (the surface facing away from the closed end $V_2$ of the vault V) to define a socket to house the device 3, where an outline of the socket corresponds substantially to the geometric line of the device 3, projected in a plane perpendicular to the axis X-X.

In some embodiments, in a second phase of the surgical procedure, the surgeon manipulates the device 3 into position. With the glenoid joint component 2 absent, the surgeon introduces the body 4 into the fossa F, substantially aligning the axes X-X and $V_1$, until the body is positioned, e.g., as shown FIG. 3. In some embodiments, and as shown in FIG. 3, the arms 6 are thereby positioned or housed in the fossa F, with the surface 62 of the arms 6 resting against the face $V_4$ of the wall $V_3$ of the vault V. The convex geometry of the contact surfaces 62 is such that the surfaces 62 hug the face $V_4$ of the vault V, extending toward the end border $V_5$ and the periphery of the closed end $V_2$ of the vault V. By way of an advantageous option, the material connecting each of the arms 6 and the body 4 may have a certain capacity for flexible, or elastic deformation, so as to encourage the spatial adaptation of these arms to the vault V.

If appropriate, during the placement of the body 4 and of the arms 6 inside the fossa F, the surgeon optionally adjusts an angular position of the body 4 about the axis X-X to maximize an area of contact between the various contact surfaces 62 and the peripheral wall $V_3$ of the vault V. In some embodiments, the arms 6 are distributed unevenly about the body 4 to better suit the non-circular interior profile of the glenoid vault V.

In some embodiments, prior to or after the body 4 and the arms 6 are positioned in the fossa F, the screw 5 is introduced into the body 4 from the end 42 such that the shank 51 projects axially from the shank end 41 and the projecting portion of the shank 51 is screwed into the bony matter of which the closed end $V_2$ of the vault V is formed. This screwing into the bone, combined with the fact that the head 52 of the screw 5 is resting against the shoulder 43 of the body 4 facilitates, firstly, a primary attachment of the device 3 in relation to the glenoid cavity G and, secondly, the surfaces 62 of the arms 6 to be pressed firmly against the wall $V_3$ of the vault V. The device 3 thus finds itself firmly immobilized in relation to the glenoid cavity G, while at the same time being positioned such that it is centered on the axis $V_1$ of the vault V (e.g., even if the glenoid cavity is locally worn). In some embodiments, the device 3 is then in the configuration depicted in FIG. 3.

In some embodiments, in a third phase of the surgical procedure, the surgeon introduces a spongy bone graft 7 into the fossa F. Generally, the graft 7 is of a consistency that is malleable enough that it can be placed all around the body 4, particularly in the empty passages 63 between the arms 6 such that the graft 7 is able to reach the region of the closed end $V_2$ of the vault V as desired. Thus, in some embodiments, the empty peripheral space E between the body 4 and the wall $V_3$ of the vault V is thus filled with the graft 7 as depicted in FIG. 4. As applicable, the presence of the graft 7 helps improve secondary attachment of the device 3 to the glenoid cavity G.

In some embodiments, in a fourth phase of the surgical procedure, the surgeon attaches the glenoid joint component 2 to the device 3 and fixedly connects it to the body 4, by fitting the peg 23 frustoconically into the end of the shank 42 as shown in FIG. 4.

In some embodiments, in use, the shoulder prosthesis 1 is mechanically loaded by the head of the humerus associated with the shoulder blade S. The arrows 6 in FIG. 4 indicate the means by which the component 2 transmits mechanical stress from the body 4 to the vault V, and in particular the peripheral wall $V_3$ through the pressing surfaces 62. As shown, the mechanical stress is spread over a large contact area and is borne by a cortical structural part of the glenoid cavity G, making the attachment of the component 2 particularly strong. In other words, risk of the component becoming detached is reduced or is otherwise substantially prevented according to some embodiments.

In some embodiments, the body 4 and/or the face 22A of the component 2 are adapted, or otherwise sized and shaped, to keep the peripheral region of the face 21A pressed only lightly against the free end border V.sub.5 of the vault V, or even at a distance from the border as depicted in FIG. 4. Generally, such an arrangement is not detrimental to the mechanical integrity of the prosthesis 1 because the arms 6 provide sufficient structural attachment to anchor the prosthesis firmly in relation to the glenoid cavity G. On the other hand, by ensuring that the face 21A of the component 2 presses little if at all against the end border V.sub.5, it is possible to reduce the potential for weakening of the end border through the creation of rims or depressions in the end border which, in the long term, detract from the mechanical integrity of the vault V and can even lead to the prostheses 1 becoming detached.

FIG. 5 shows another shoulder prosthesis 1' including a component 2' and the device 3. In some embodiments, the shoulder prosthesis 1' optionally is characterized as a reverse shoulder prosthesis intended to collaborate with a prosthetic humeral component with a concave joint face that complements the face 22A'. In particular, in the prosthesis 1', the component 2 with a concave joint face 22A is replaced by a component 2' having a joint face 22A' which is convex and an opposite face 21A' that is functionally analogous to the face 21A of the component 2. The face 21A' is optionally configured to facilitate fixedly attaching the component 2' to the attachment device 3 via a substantially frustoconical fitting, such as the peg 23 of the device 2.

FIGS. 6 and 7 show another device 13 similar to the device 3. In some embodiments, the device 13 differs from the device 3 in that the device 3 has fewer arms 16 and/or the arms 16 are not made as one piece with its tubular body 14, the arms 16 being otherwise secured to the body 14. For example, as shown, the device 13 includes three arms 16 borne by a support ring 18, also described as a support member, the support ring 18 being a separate piece from the body 14. In some embodiments, and as shown, the arms 16 are optionally formed as an integral part of the ring 18 such that the ring 18 joins together the ends of the arms 16 the free ends 161 of the arms 16. The ring 18 is optionally sized to be attached inside the body 14, being centered on the axis X-X of the body, as depicted in FIG. 7. For example, the ring 18 is adapted to be introduced into the body 14, from an axial end 142 of the body 14 which is opposite to the end 141 that faces towards the closed end V.sub.2 of the vault V.

In some embodiments, in order to allow the ring 18 to fit into the body 14 until it rests axially against an internal shoulder 143 of the body 14, the body 14 defines straight through-slots 145, parallel to the axis X-X, each through-slot 145 being shaped to accommodate a corresponding one of the arms 16. Each slot 145 extends from the shoulder 143 as far as the end 142 of the body 14 such that each slot defines an open end opposite the shoulder 143.

In some embodiments, in addition to the screw 5 described above, the device 13 comprises a sleeve 19 designed to be attached coaxially inside the body 14, more specifically inside the end 142 thereof, with the ring 18 axially interposed between the sleeve 19 and the shoulder 143, as depicted in FIG. 7. The bore of the sleeve 19 defines a shoulder 191 towards an end of the sleeve that abuts the ring 18. Upon receiving the screw 5 through the bore, the head 52 of the screw 5 abuts the shoulder 191, or rests axially against the shoulder 191, as shown in FIG. 7. Opposite the shoulder 191, the bore forms a frustoconical surface 192 which, when the sleeve 19 is assembled with the body 14, is centered on the axis X-X and converges towards the end 141 of the body 14. In some embodiments, the shoulder 191 and the frustoconical surface 192 function analogously to the shoulder 43 and to the frustoconical surface 44 of the attachment device 3, with respect to the screw 5 and to the glenoid joint component 2 or 2', respectively.

Some methods of attaching the component 2 or 2' to the glenoid cavity G proceed as follows. Having opened access to the vault V of the glenoid cavity G, the surgeon introduces the body 14 into the fossa F, more or less aligning the axes X-X and V.sub.1, if necessary until the end 141 of the body is resting against the closed end V.sub.2 of the vault V. The surgeon then introduces the ring 18, the sleeve 19 and the screw 5 in turn into the interior of the body 14, passing them through the body end 142. Progression from the ring 18 as far as the shoulder 143 optionally entails fitting each of the arms 16 into one of the slots 145. To make the relative angular positioning of the body 14 and the ring 18 easier, the end 142 of the body is advantageously provided with visual identification protrusions 146.

In some embodiments, screwing the shank 51 of the screw 5 into the bony matter of which the closed end V.sub.2 of the vault V is formed fixes the assembly of the various components of the device 13 while at the same time providing the primary attachment of the device 13 in relation to the glenoid cavity G and pressing the opposite surfaces 162 of the arms 16 to the body 14 against the wall V.sub.3 of the vault V. In some other embodiments, the ring 18 and the sleeve 19 are be added into the body 14 before the body 14 is introduced into the fossa F.

In some embodiments, the fitting of a shoulder prosthesis comprising the component 2 or 2' and the device 13 is completed by next attaching the glenoid joint component 2 or 2' to the device 13 using the frustoconical insertion in the sleeve 19. If appropriate, the first and third phases of the surgical procedure previously mentioned are implemented as desired during fitting.

In still other embodiments of the attachment devices 3 and 13, the arms 6 or 16 are respectively connected to the body 4 or to the ring 18 by articulated mechanical means designed to allow each arm to pivot with respect to the body about an axis of articulation that is orthoradial to the axis X-X. The pivoting of the arms 6 or 16 about the aforementioned axes is then advantageously brought about by the screw 5 when the latter is introduced through the end 41 or 141 of the body 4 or 14 to be screwed into the closed end V.sub.2 of the vault V. The force with which the arms 6 or 16 are anchored in relation to the glenoid cavity G are adjusted as desired by the surgeon using the screw 5.

Figure 8:
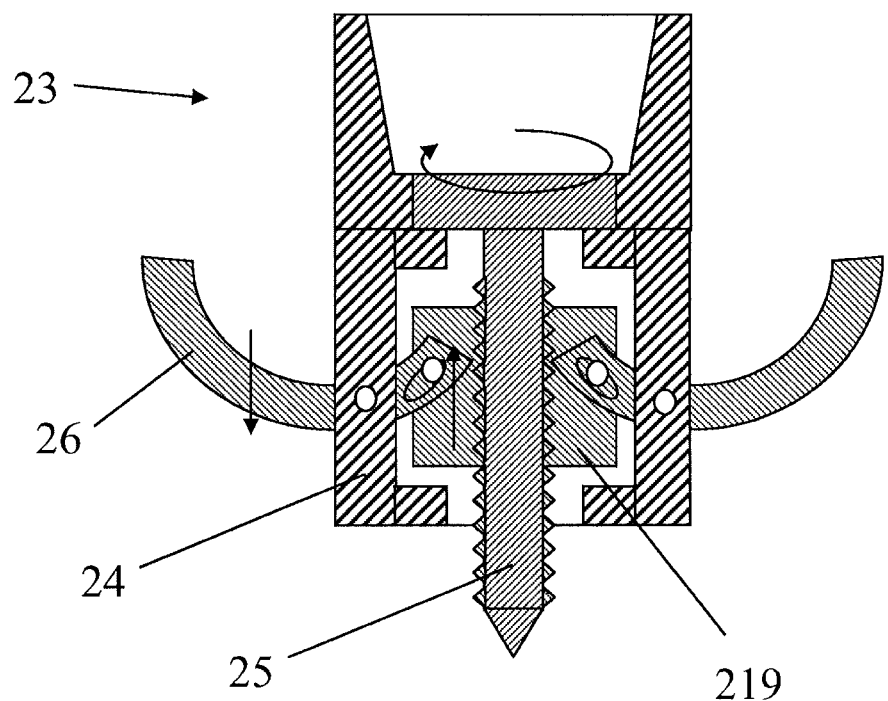
FIG. 8 is a schematic view of another attachment device, according to some embodiments.

FIG. 8 shows another device 23 including a body 24, a screw 25, arms 26, and a sleeve 219, where the arms 26 articulate mechanically upon turning of screw 25. In particular, the arms 26 are pivotably engaged with the body 25 and a sleeve 219. The sleeve 219 is engaged with the screw 25 such that the sleeve 219 moves axially along the screw 25 upon turning the screw 25. As shown, the arms 26 are thereby optionally deployed using the screw 25 according to some embodiments.

In still other embodiments, provision is made for the arms 6 or 16 to be connected to the body 4 or 14 of one and the same attachment device similar to the devices 3 or 13 using types of connection that differ from one another, chosen from among those described above, namely from a rigid connection, a connection with flexible deformation of material, and a connection that is mechanically articulated.

In practice, the body 4 or 14 and the arms 6 or 16 and, where appropriate, the ring 18 and the sleeve 19, are made of materials that are able to withstand the mechanical stresses described above while at the same time affording a lasting connection between them that is either rigid or elastically deformable or articulated as mentioned previously. Thus, they may be made of metal or a polymer, it being pointed out moreover that the materials of which the body 4 and the arms 6 are respectively made optionally have different compositions. Where use is made of a polymer, the latter is advantageously bioresorbable. If use is made of a metal alloy, the latter may advantageously be a shape memory alloy, for example, making it possible, when the body 4 or 14 is being placed inside the fossa F, for the curved longitudinal profile of the arms 6 to be modified through a shape memory effect in order to strengthen the anchorage of the device 3 or 13 in relation to the glenoid cavity G.

In various embodiments, the material chosen from which to make the body 4 or 14 and the arms 6 or 16 is advantageously porous, to encourage the secondary attachment by bone regrowth. Furthermore, the bone regrowth is also encouraged by ensuring that the body and the arms have a holed solid structure encouraging biological exchanges within the fossa F as previously described.

In some embodiments, rather than mating by frustoconical fitting, the end 42 of the body 4 or the sleeve 19 and the face 22A or 22A' of the glenoid joint component 2 or 2' are optionally fixably attached together by different complementing shapes, such as a dovetail shape. Furthermore, to supplement or to replace fixation through complementing shapes, a fastener is optionally added between the components, such as a screw.

In some embodiments, the cross section of the arms 6 or 16 may have an exterior outline of a shape other than that of a square, provided that, on the opposite side to the body 4 or 14, each arm 6 or 16 has a surface for resting against the internal face V.sub.4 of the wall V.sub.3 of the vault V adapted to contact the vault V, e.g., analogously to the contact surfaces 62 or 162 described above. Moreover, by way of option, each of these contact surfaces has, particularly in the longitudinal direction of the arm 6 or 16, a profile involving teeth and troughs to improve the purchase of the surface on the wall V.sub.3 of the vault V.

In some embodiments, the number of arms 6 or 16 is not limited to four or three, it being understood that, for reasons of stability, generally three or more arms are contemplated to ensure three separate contact regions (e.g., five or more arms are possible). Additionally, the screw 5 for fastening into the bone may be replaced by any analogous fastening means able to collaborate with the end 41 or 141 of the body 4 or 14.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical method of attaching a joint component to a socket in an anatomy, the method comprising:
   accessing the socket in the anatomy;
   introducing a support body into the socket such that a first end of the support body is positioned toward an open end of the socket, a second end of the support body is positioned toward a closed end of the socket, and the support body is spaced from a peripheral wall of the socket;
   positioning a support member in the support body, the support member having a plurality of contact arms;
   pressing the plurality of contact arms against an internal face of the peripheral wall of the socket to secure the support body in the socket, each of the plurality of contact arms being spaced apart from an adjacent one of the contact arms to form a plurality of passages about the support body to the peripheral wall of the socket;
   passing a screw through the support body and the support member and fixing the screw into bone defining the socket; and
   attaching a joint component to the first end of the support body.

2. The surgical method of claim 1, further comprising filling the plurality of passages and the space between the body and the socket with a spongy bone graft to encourage secondary fixation of the support body to the socket.

3. The surgical method of claim 1, wherein pressing the plurality of contact arms against the internal face forms a plurality of passages past the body to the closed end of the socket.

4. The surgical method of claim 1, further comprising removing bone from the anatomy to form the socket in the anatomy.

5. The surgical method of claim 4, wherein the socket is formed in a glenoid cavity of a shoulder blade.

6. The surgical method of claim 1, wherein pressing the plurality of contact arms against the internal face further includes pressing a plurality of porous contact arms against the internal face of the peripheral wall to encourage secondary attachment by bone regrowth.

7. The surgical method of claim 1, wherein pressing the plurality of contact arms against the internal face further includes elastically deforming the plurality of contact arms against the internal face of the peripheral wall to strengthen anchorage of the support body to the socket in the anatomy.

8. The surgical method of claim 1, wherein attaching a joint component to the first end of the body includes attaching a shoulder joint component having a concave articulating surface.

9. The surgical method of claim 1, wherein attaching a joint component to the first end of the body further includes attaching a shoulder joint component having a convex articulating surface.

10. The surgical method of claim 1, wherein attaching a joint component in the first end of the body further includes positioning a shank of the joint component into a tapered bore of a sleeve extending into the first end of the support body to secure the joint component to the support body.

11. A surgical method of attaching a joint component to a socket in an anatomy, the method comprising:
    opening access to soft tissue surrounding a joint;
    removing bone to form the socket in the anatomy at the joint having an open end, a closed end, and a peripheral wall;
    positioning a support body having a plurality of spaced apart contact arms extending securely from a support ring positioned within the support body into the socket such that the plurality of contact arms engage the peripheral wall to secure the support body in the socket and form spaces between each of the plurality of spaced apart arms and the support ring; and
    attaching a joint component to the support body;
    wherein each of the plurality of contact arms extends from a first fixed end attached to the support ring to a second free end cantilevered from the support ring; and wherein positioning the plurality of contact arms includes elastically deforming the plurality of contact arms against the peripheral wall to radially displace the second free ends and to strengthen anchorage of the support body to the socket in the anatomy.

12. The surgical method of claim 11, wherein the socket is formed in a glenoid cavity of a shoulder blade.

13. The surgical method of claim 11, wherein positioning the plurality of contact arms further includes pressing a plurality of porous contact arms against the peripheral wall to encourage secondary attachment by bone regrowth.

14. The surgical method of claim 11, wherein attaching a joint component to the body further includes positioning a shank of the joint component into a tapered bore extending into the support body to secure the joint component to the support body.

15. The surgical method of claim 14, wherein attaching the joint component to the support body with a taper connection further includes attaching a shoulder joint component to the support body where the shoulder joint component includes one of either a concave articulating surface or a convex articulating surface.

16. A surgical method of attaching a joint component to a socket in an anatomy, the method comprising:

forming the socket in a shoulder joint of the anatomy;
extending a plurality of spaced apart contact arms of a support ring through a support body;
pressing the plurality of spaced apart contact arms of the support ring into the socket such that each contact arm engages an internal face of the socket to secure the support body in the socket;
inserting a fastener shank through the support ring to project axially from the support body; and
attaching a shoulder joint component to the support body where the shoulder joint component includes either a concave or a convex articulating surface.

17. The surgical method of claim 16, wherein each of the contact arms extends from a first end coupled to the support ring to a second flat free end separate from the support body and support ring to engage the internal face of a peripheral wall of the socket.

18. The surgical method of claim 16, wherein forming the socket in a shoulder joint of the anatomy further includes forming the socket in a glenoid cavity of the shoulder joint.

19. The surgical method of claim 11, further comprising extending a fastener through the support ring and the support body and into the socket.

* * * * *